United States Patent [19]

Reynolds

[11] Patent Number: 5,213,104
[45] Date of Patent: May 25, 1993

[54] DOPPLER ULTRASOUND MONITOR SYSTEM

[76] Inventor: Charles A. Reynolds, 11 Shingle Hill Rd., West Haven, Conn. 06516

[21] Appl. No.: 782,142

[22] Filed: Oct. 24, 1991

[51] Int. Cl.⁵ ............................................. A61B 8/06
[52] U.S. Cl. ........................... 128/661.07; 128/661.09
[58] Field of Search .......... 128/660.05, 661.07–661.10

[56] References Cited

U.S. PATENT DOCUMENTS

| | | |
|---|---|---|
| 3,792,613 | 2/1974 | Couture . |
| 3,910,259 | 10/1975 | Sullivan . |
| 4,065,960 | 1/1978 | Grabendorfer et al. . |
| 4,117,446 | 9/1978 | Alais . |
| 4,158,308 | 6/1979 | Sharpe et al. . |
| 4,310,907 | 1/1982 | Tachita et al. . |
| 4,324,258 | 4/1982 | Huebscher et al. ............ 128/661.09 |
| 4,357,944 | 11/1982 | Mauser et al. . |
| 4,373,533 | 2/1983 | Iinuma ........................... 128/660.05 |
| 4,375,166 | 3/1983 | Auphan . |
| 4,383,533 | 5/1983 | Bhagat et al. . |
| 4,391,144 | 7/1983 | Diederichs . |
| 4,412,248 | 10/1983 | Carmen . |
| 4,485,821 | 12/1984 | Iinuma . |
| 4,534,357 | 8/1985 | Powers . |
| 4,543,826 | 10/1985 | Ferrari . |
| 4,554,926 | 11/1985 | Shirasaka . |
| 4,607,642 | 8/1986 | Powers . |
| 4,699,009 | 10/1987 | Masiak et al. . |
| 4,744,367 | 5/1988 | Kodama et al. . |
| 4,755,953 | 7/1988 | Geithman et al. . |
| 4,817,617 | 4/1989 | Takeuchi et al. ............ 128/660.05 |
| 4,866,613 | 9/1989 | Amemiya et al. . |
| 4,873,985 | 10/1989 | Nakajima ...................... 128/660.05 |
| 4,890,624 | 1/1990 | Ganguly et al. . |

Primary Examiner—Francis Jaworski
Attorney, Agent, or Firm—Darby & Darby

[57] ABSTRACT

A multi-transducer Doppler ultrasound monitor system is disclosed in which a multiplexed switch is interposed between the ultrasound transducers and a single transmitter and receiver of the type utilized used to drive a single transducer and to process the signal produced by that transducer, respectively. This switch has a plurality of inputs, each of which receives a connection to one of the transducers, and a single output which is connected to the transmitter and receiver, and it is effective to connect each input, in sequence, to the output on a time-shared basis. A track & hold circuit is provided at the output of a demodulator following the receiver. This circuit has a single input and a plurality of outputs, each corresponding to one of the multiplex switch inputs. The track & hold circuit distributes the signal at the output of the demodulator in sequence to each of the circuit outputs. In this manner, a single set of electronics can be utilized for a plurality of transducers.

5 Claims, 3 Drawing Sheets

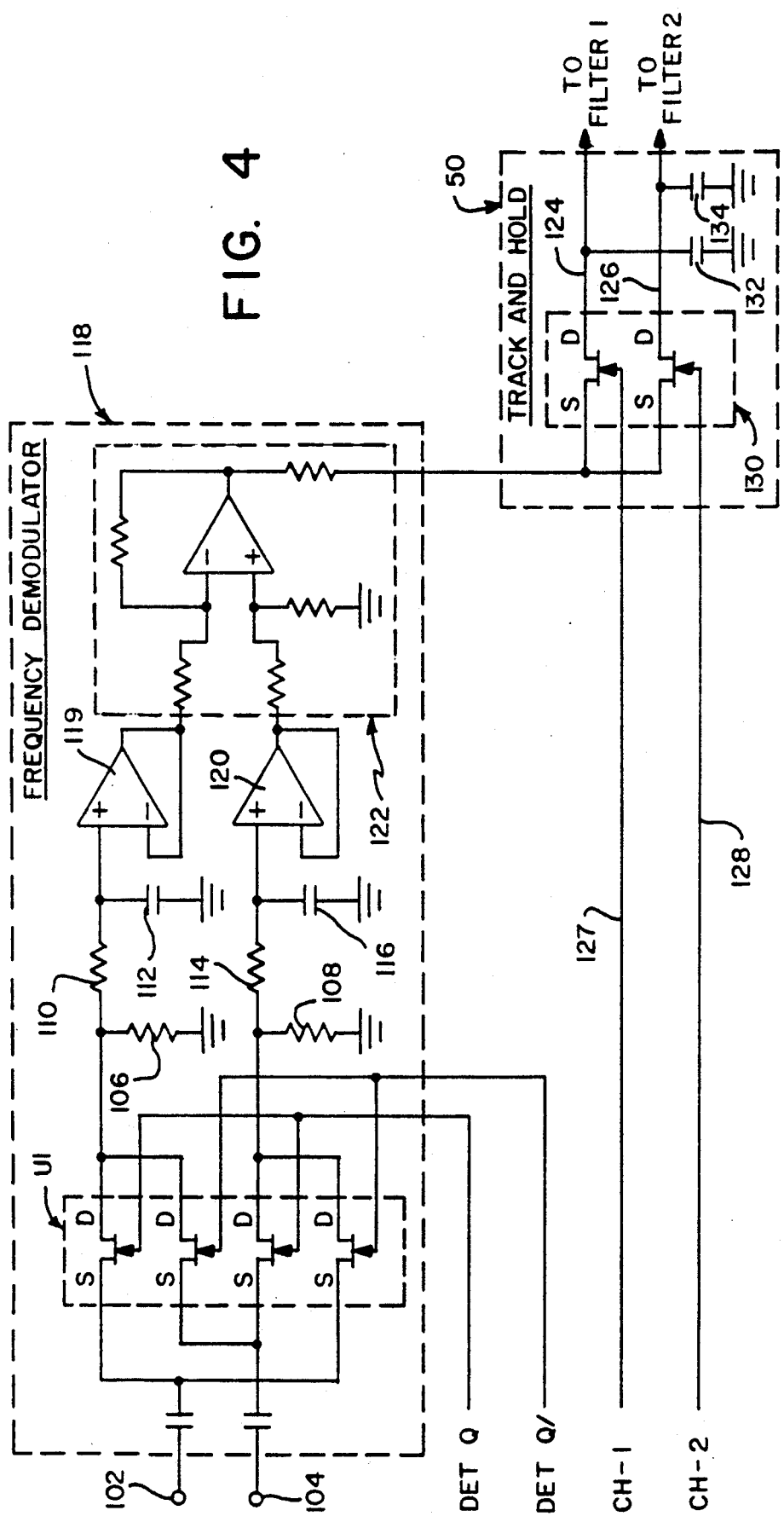

DOPPLER ULTRASOUND MONITOR SYSTEM

FIELD OF THE INVENTION

The present invention relates generally to doppler ultrasound monitoring systems and, more particularly, concerns medical applications therefor, such as heart-rate monitors and blood flow monitors.

BACKGROUND OF THE INVENTION

Doppler ultrasound monitoring systems operate on the principal that ultrasound energy incident upon a moving surface is reflected by that surface and experiences a change of frequency which is proportional to the rate of movement of the surface. The most widespread medical applications for doppler ultrasound monitoring systems have occurred in blood flow analysis (the ultrasound is reflected from flowing blood) and heart rate analysis (the ultrasound is reflected from one or more appropriate surfaces of the heart).

Often, it is desirable to utilize multiple ultrasound transducers so that measurements can be taken at two different locations or from two different angles. Typically, this has engendered substantial expense or substantial complications which affect the reliability of measurements. While ultrasound transducers are relatively inexpensive, the electronic equipment which drives the transducer and senses the signal that the transducer produces can be relatively complex and expensive. Furthermore, the electronics associated with different probes can have characteristics which are quite different, such as different degrees of phase shift. Moreover, these differences can change with environmental conditions, such as temperature and with time. Accordingly, the electronics can require frequent or constant calibration in order to assure accurate results.

Basically, it is an object of the present invention to avoid the shortcomings of existing multi-transducer Doppler ultrasound monitoring systems. It is specifically an object to reduce substantially the amount of electronic equipment required to operate a plurality of ultrasonic sensors in a Doppler ultrasound monitoring system.

It is also an object of the present invention to eliminate the need for relative calibration of the electronics utilized to drive a plurality of ultrasound transducers and to sense the signals produced thereby.

It is another object of the present invention to provide a multi-transducer Doppler ultrasound monitoring system which is convenient and reliable in use, yet relatively inexpensive and simple in operation.

In accordance with the present invention, a multiplexed switch is interposed between a plurality of ultrasound transducers and a single transmitter and receiver of the type utilized to drive a single transducer and to process the signal produced by that transducer, respectively. This switch has a plurality of inputs, each of which receives a connection to one of the transducers, and a single output which is connected to the transmitter and receiver, and it is effective to connect each input, in sequence, to the output on a time-shared basis. In addition, a track & hold circuit is provided at the output of the electronics. This circuit has a single input and a plurality of outputs, each corresponding to one of the multiplex switch inputs. The track & hold circuit senses the signal at the output of the electronics and distributes it in sequence to each of the outputs. In this manner, a single set of electronics can be utilized for a plurality of transducers, thereby eliminating the cost of additional electronics, as well as the need for relative calibration of the electronics for different transducers.

BRIEF DESCRIPTION OF THE DRAWING

The foregoing brief description, as well as further objects, features and advantages of the invention will be understood more completely from the following detailed description of presently preferred, but nonetheless illustrative, embodiments of the invention, with reference being had to the drawings, in which:

FIG. 4 is a functional schematic diagram illustrating a preferred embodiment for track & hold circuit 50 of FIG. 2, and a preferred frequency demodulator 118.

DETAILED DESCRIPTION

Figure 1:
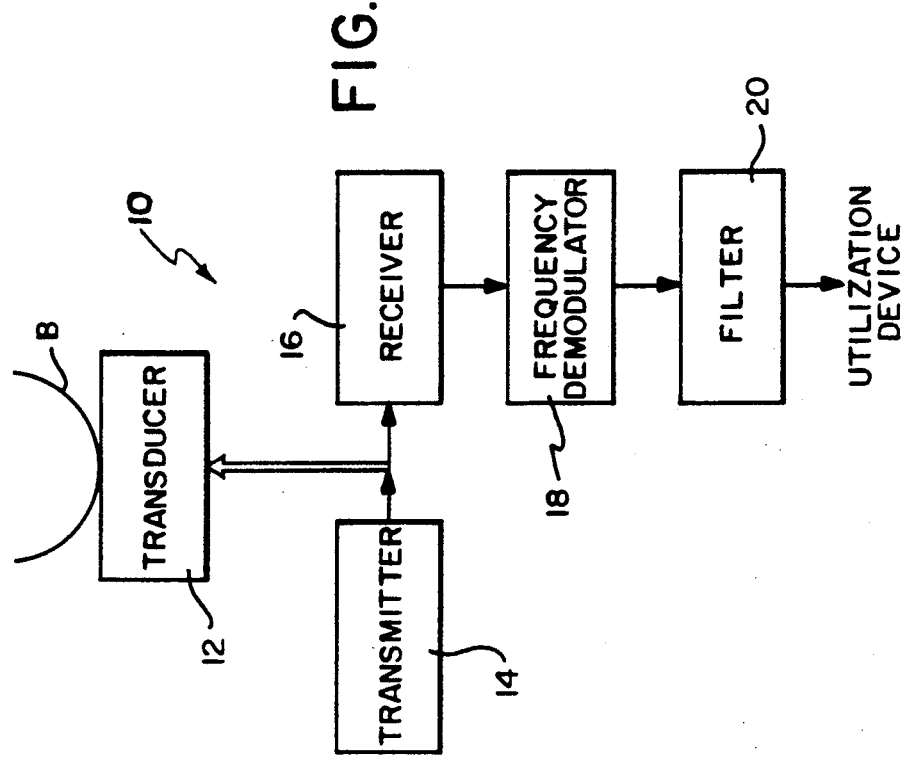
FIG. 1 is a functional block diagram illustrating a conventional ultrasound monitoring system.

Turning now to the details of the drawings, FIG. 1 is a functional block diagram illustrating a conventional Doppler ultra-sound monitor system. The device operates on the principle that ultrasound energy incident upon a moving surface will be reflected thereby, and the reflected ultrasound signal will experience a change in frequency which is proportional to the rate of movement of the surface.

FIG. 1 illustrates such a monitor system 10 including a transducer 12 in contact with a living body B, within which heart rate is to be detected. Transducer 12 is a conventional ultrasonic transducer which may be electrically excited to generate ultrasound energy, and, in response to incident ultrasound energy, emits an electrical signal.

An electrically actuated transmitter 14 is electrically coupled to transducer 12 and, when actuated, causes the transducer to emit ultrasonic energy. On the other hand, when ultrasonic energy impinges on transducer 12, the transducer emits an electrical signal which is coupled to receiver 16. This signal is an electrical representation of the ultrasonic energy incidence on transducer 12 and, therefore, has a frequency variation which is proportional to the rate of movement of the incident surface in the body (in this case, on appropriate wall of the heart). This electrical signal is appropriately filtered and amplified by receiver 16 and is supplied therefrom to a frequency demodulator 18, which, as is well-known, produces a demodulated signal which both amplitude (e.g. voltage) and frequency information. The demodulated signal therefore be used to obtain a direct indication of heart rate. After filtering by main filter 20, which provides a degree of cleaning or smoothing, the signal is in appropriate condition for application to a utilization device, such as some form of display or meter.

In FIG. 1, transducer 12 is coupled to transmitter 14 and receiver 16 through a double line. As a convention, such a line will represent a duplex connection. That is, one in which signals flow in both directions. In contrast, a single line will represent a connection in which signal flow is in one direction, usually indicated by an arrowhead.

Figure 2:
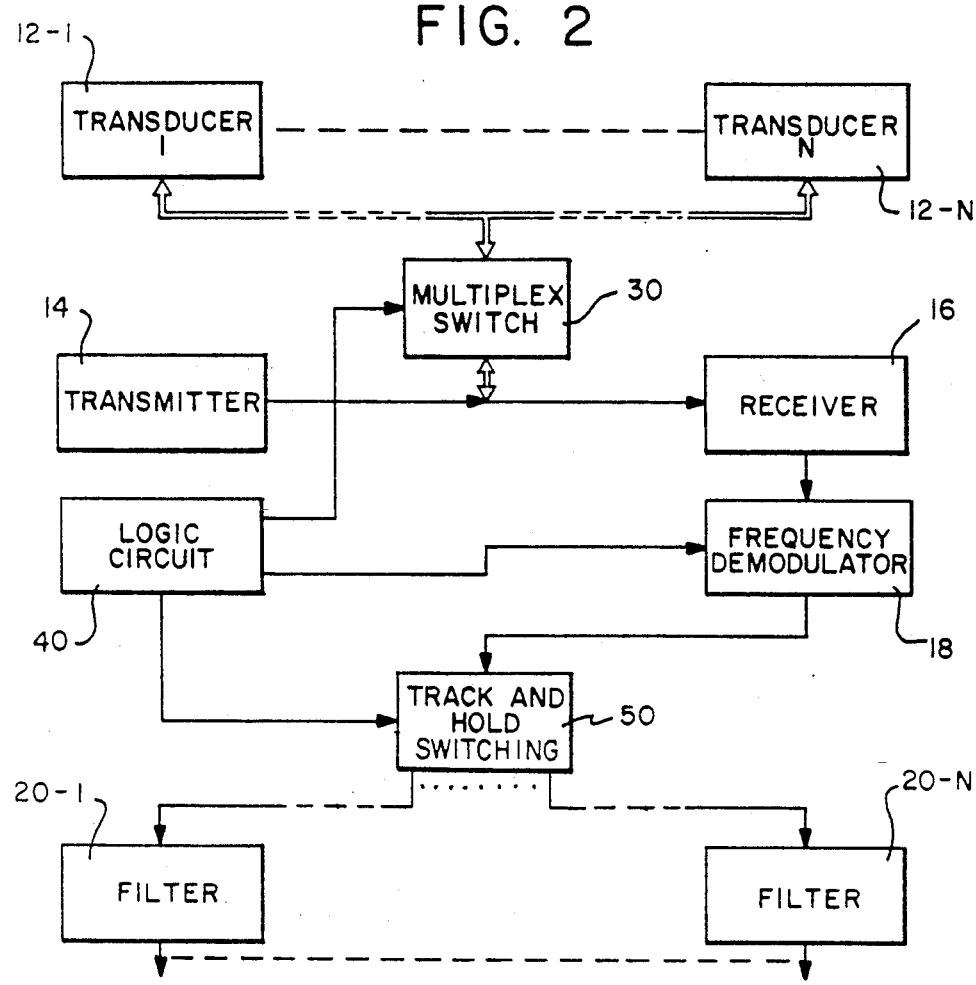
FIG. 2 is a functional block diagram similar to FIG. 1 illustrating an ultrasound monitoring system utilizing a plurality of transducers in accordance with the present invention.

FIG. 2 is a functional block diagram illustrating the basic structural concept of the present invention. In this block diagram, those elements which are similarly numbered to elements in FIG. 1, namely transmitter 14, receiver 16, and frequency demodulator 18, can be assumed to be identical. In addition, the ultrasound monitor in accordance with FIG. 2 includes N transducers 12-1 through 12-N which are identical to transducer 12 of FIG. 1, and it also includes N filters, filters 20-1 through 20-N which are identical to main filter 20 of FIG. 1.

A multiplex switch 30 is interposed between transducers 12-1 through 12-N and the connection between transmitter 14 and receiver 16. In addition, a track & hold circuit 50 is interposed between frequency demodulator 18 and filters 20-1 through 20-N. The multiplex switch 30 and the track & hold circuit 50 are controlled by a logic circuit 40, and transmitter 14 is driven thereby.

In operation, the system of FIG. 2 permits the accommodation of a plurality of transducers, while utilizing only a single transmitter, receiver and frequency demodulator. Logic circuit 40 operates multiplex switch 30 so that, on a repetitive basis, transducers 12-1 through 12-N are connected, in turn, to the junction between transmitter 14 and receiver 16. At the same time, logic circuit 40 operates track & hold circuit 50 so that, at any instant, the filter receiving the signal from frequency demodulator 18 is the appropriate one corresponding to the transducer which is connected to transmitter 14 and receiver 16. In this manner, the transmitter, receiver, and frequency demodulator are time-shared among the transducers and the corresponding filters.

Figure 3:
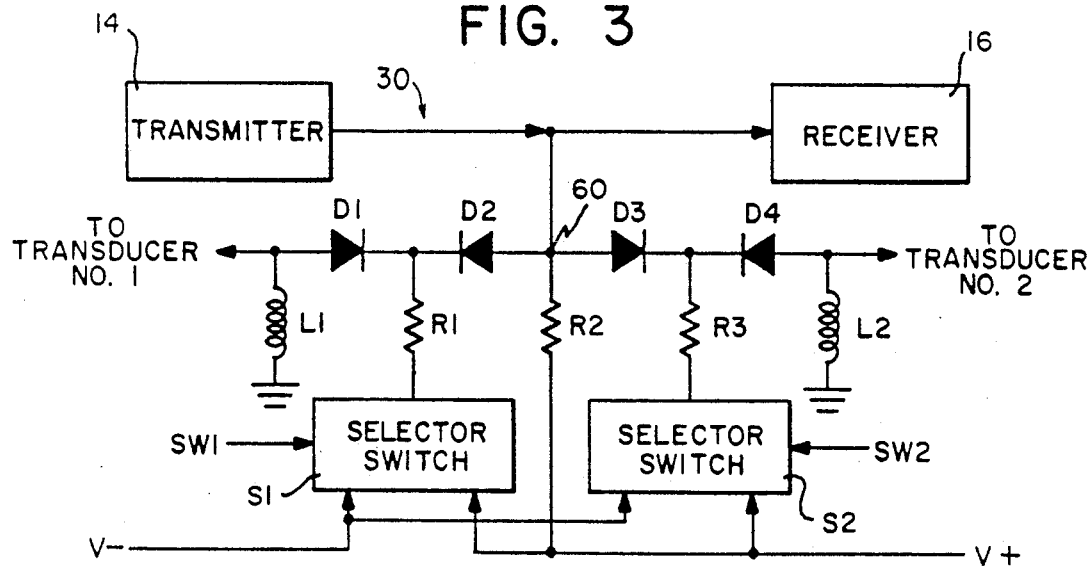
FIG. 3 is a functional schematic diagram illustrating a preferred embodiment for multiplex switch 30 of FIG. 2.

FIG. 3 is a schematic diagram demonstrating the details of multiplex switch 30 of FIG. 2. For illustrative purposes, a switch for use with two transducers has been illustrated. However, those skilled in the art will appreciate that the same structural concept is readily extended to three or more transducers.

Switch 30 makes use of two power supplies V+ and V−, which are relatively high in amplitude compared to the signals provided to and received from the transducers. As was the case in FIG. 2, elements designated by the same reference character as in preceding figures, namely transmitter 14 and receiver 16, can be assumed to be identical to the same elements in preceding figures.

Multiplex switch 30 comprises 2 switching subunits, each of which includes an inductor, two PIN diodes, a resistor, and a selector switch. For example, one unit comprises the elements indicated as L1, D1, D2, R1, and S1, whereas the second unit comprises the elements L2, D3, D4, R3 and S2. In each of the switching units, the inductor is grounded at one end, and the corresponding transducers is connected to the other end of the inductor. Each of the selector switches is connected to positive power supply V+ and negative power supply V−, which are selected in amplitude so as to be substantially larger than the signals produced by transmitter 14 or the transducers. In addition, switch S1 is controlled by a Signal SW1 and switch S2 is controlled by a Signal SW2, which signals are discussed further below.

Switches S1 and S2 are conventional selector switches (see selector switch 130 below) which have the characteristic that when the control signal (i.e., SW1 or SW2) is in a low state, they pass the voltage V−, whereas when the control signal is in the high state, they pass the voltage V+. One requirement of the signals SW1 and SW2 is that they cannot both be in the low state at the same time.

Operation will be illustrated by assuming that SW2 is in the low state and SW1 is in the high state. Under these circumstances, V− appears at the bottom of R3 and diodes D3 and D4 are biased on. Diode D3 is biased on via V+ through R2, D3 and R3, and diode D4 is biased on via ground through L2, D4 and R3. In addition, SW1 will be in the high state, so that V+ is applied to the bottom of R1. This causes both D1 and D2 to be back biased. With these switches (SW1 and SW2) in this condition, transducer 1 is isolated from node 60 and transducer 2 is connected to node 60, so that it has full access to transmitter 14 and receiver 16. Those skilled in the art will appreciate that, when SW1 and SW2 subsequently change state, that is, when SW1 goes high and SW2 goes low, transducer 2 will be isolated from node 60 and transducer 1 will be connected to node 60. Accordingly, transducers 1 and 2 are alternately connected to and isolated from transmitter 14 and receiver 16.

FIG. 4 is a schematic circuit diagram illustrating the details of a preferred form of track and hold circuit 50 and a preferred embodiment 118 of frequency demodulator 18. Again, a system utilizing two filters is illustrated, but it should be clear that those skilled in the art could readily extend the system to include three or more filters.

Frequency demodulator 118 is assumed to be driven by a receiver which provides a differential output, and therefore it includes differential inputs 102, 104 which are capacitively coupled so as to block any DC signals. The differential input signals are provided to an integrated circuit U1, which is a quad high speed analog switch configured as a balanced ring demodulator. The FET switches in circuit U1 are controlled by the signals DET Q and DET Q/, which are described further below. At this point, it should be sufficient to state that these two signals are at the same frequency as the signal produced by transmitter 14, but of opposite phase.

At each of the outputs of U1, there is provided a resistor connected to ground, 106 and 108 respectively. In addition, each output of U1 is connected in series with a resistor, 110 and 112, respectively, the opposite end of which is connected to ground through a capacitor, 112 and 116 respectively. Resistors 110 and 114 are also each connected to unity gain amplifier 119 and 120 respectively, which isolate capacitors 112 and 116 from the circuitry which follows. That circuitry comprises an amplifier 122, which provides 26 dB of gain. As explained above, capacitors 112 and 116 are part of an averaging circuit. Resistors 106 and 108 are provided to discharge the capacitors when the switches of U1 turn off. This assures that the capacitors will be ready to average the next signal arriving, which will correspond to another transducer.

The output of amplifier 122 is applied to track and hold circuit 50. In operation, DET Q and DET Q/ are at the same frequency as the signal produced by transmitter 14. Should the transducer coupled with demodulator 118 return an unmodified frequency, there would, at most, be a phase shift between the signals controlling U1 and the returning signal from the transducer.

Through the averaging action of resistor 110 and capacitor 112 and resistor 114 and capacitor 116, this would produce some DC voltage at the inputs to amplifiers 119 and 120, but this voltage would not be detected, because of A.C. coupling. On the other hand, should the transducer return a frequency which varies, a time-varying differential signal is produced between amplifiers 119 and 120, so that amplifier 122 produces an output signal.

Track and hold circuit 50 includes an analog selector switch 130, which receives the signal from frequency demodulator 118 as an input. The selector switch also includes a pair of outputs 124 and 126, and a pair of control inputs 127 and 128. Output 124 is provided to filter 1 and is also connected to ground through a capacitor 132, and output 126 is provided to filter 2 and is also provided to ground through a capacitor 134. The signals CH-1 and CH-2 are provided to inputs 127 and 128, respectively to control selector switch 130. These signals are discussed further below. At this point it should be sufficient to say that CH-1 and CH-2 cannot be in the same state simultaneously. Those skilled in the art will appreciate that selector switch 130 may be nothing more than a portion of an integrated circuit of the same type as U1.

In operation, when one of control inputs 127, 128 goes low, the corresponding FET switch is closed and the signal at the output of frequency demodulator 118 is passed to the corresponding output. At that point, the signal of that output follows or tracks the signal at the output of demodulator 118. Subsequently, signals CH-1 and CH-2 reverse state, so that the switch which was closed is opened and visa-versa. At that point, the output which was tracking demodulator 118 is isolated from the demodulator, and the signal on the corresponding capacitor is held constant. Those skilled in the art will appreciate that by correlating the DET Q and DET Q/ with CH-1 and CH-2, signals from the appropriate transducer will be tracked and held on the corresponding one of capacitors 132 and 134 and therefore will be applied to the appropriate output filter.

Figure 5:
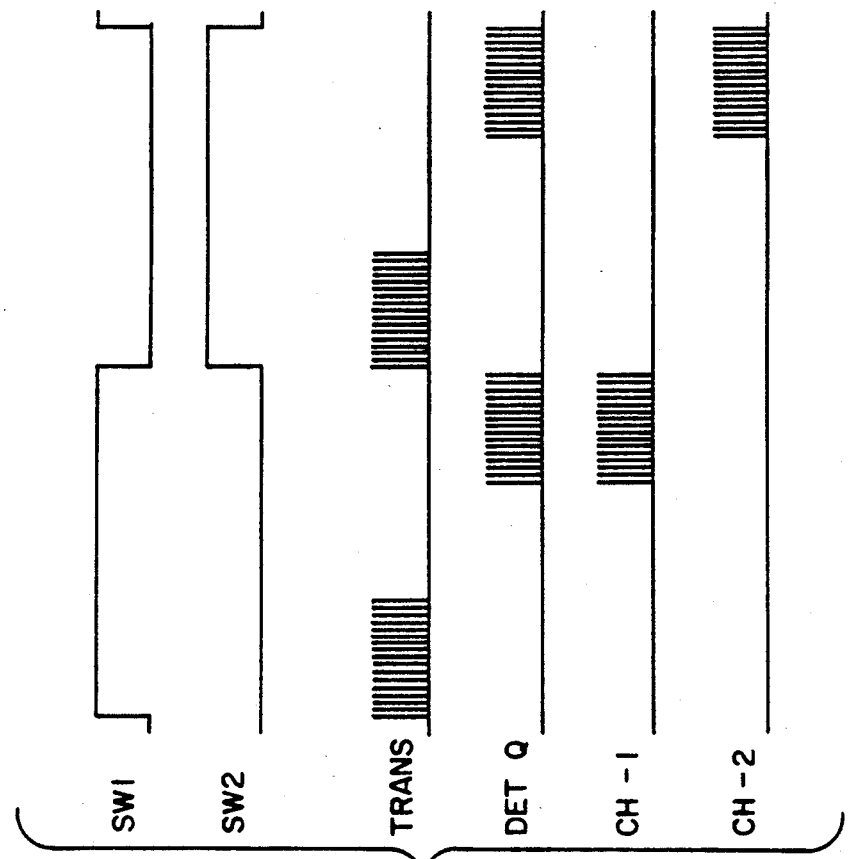
FIG. 5 is a wave form diagram useful in describing the operation of FIGS. 2–4.

Logic circuit 40 provides all of the control signals discussed previously. It also provides a signal TRANS which drives transmitter 14. In the exemplary embodiment which includes two transducers and two main filters, the signals SW1 and SW2 are two 2 KHz square waves which are one hundred and eighty degrees out of phase. Thus each of switches S1 and S2 is closed for 250 μsec. FIG. 5 is a waveform chart illustrating one cycle of each of the control signals discussed above. Signals SW1 and SW2 are out of phase square waves at 2 KHz. In each half cycle of SW1 and SW2, the signal TRANS includes a burst of a 1.151 MHz square wave which occupies approximately the first third of the half cycle. The signal DET Q includes a similar square wave burst in the last third of each half cycle of SW1, but a quiet period is provided just before the end of the half-cycle in order to avoid overlap between DET Q and TRANS. DET Q/ is the same as DET Q, but 180 degrees out of phase. Signals CH-1 and CH-2 are the same as DET Q, except that they are present only in opposite half-cycles.

From these waveforms, it will be appreciated that a channel is made available for each transducer every 500 μsec for a 250 μsec half-cycle. During each half-cycle, transmitter 14 is driven for the first third of the half-cycle. Thereafter DET Q and DET Q/ operate the demodulator 118 during the last third of each half-cycle. This allows enough time for the ultrasound to be reflected and detected. At the same time, one of the capacitors 132, 134 receives the demodulated signal, the other capacitor being isolated therefrom. Thus, each capacitor receives the demodulated signal corresponding to its transducer.

Although preferred forms of the invention have been disclosed for illustrative purposes, those skilled in the art will appreciate that many additions, modifications, and substitutions are possible, without departing from the scope and spirit of the invention as defined by the accompanying claims.

What is claimed is:

1. In a multi-transducer Doppler ultrasonic monitoring system:
   a multiplex switch having a plurality of inputs each adapted to be connected to an ultrasound transducer and a single output, said switch connecting each of said inputs to said output in sequence on a timeshared basis;
   transmitting means for providing a signal for actuating an ultrasonic transducer, said, transmitting means being connected to the output of said multiplex switch;
   receiving means connected to the output of said multiplex switch for converting a signal received from an ultrasound transducer to a demodulated output signal;
   output means responsive to and having a single input connected to said receiving means and also having a plurality of outputs, each corresponding to one of said transducers, for sequentially connecting said outputs to said input on a timeshared basis; and
   control means for controlling and coordinating the operation of said multiplex switch and said output means so that a multiplex switch input connected to the output of the multiplex switch and an output means output which is simultaneously connected to the input of the output means correspond to the same transducer.

2. A Doppler ultrasound monitor system in accordance with claim 1 wherein said control means acts on said multiplex switch so as to connect each of the inputs thereof to the output thereof during partial-cycles of equal duration and acts upon said output means to connect each output thereof to the input thereof during partial-cycles of equal duration.

3. A Doppler ultrasound monitor system in accordance with claim 2 wherein said control means actuates said transmitting means during approximately the first third of each partial-cycle.

4. A Doppler ultrasound monitor system in accordance with claim 3 wherein said output means comprises means for storing the signal at each output thereof upon the conclusion of the partial-cycle of that output.

5. A Doppler ultrasound monitor system in accordance with claim 4 wherein said control means acts upon said output means so that said means for storing store each output signal during the last third of the corresponding partial-cycle.

* * * * *